United States Patent [19]

Mescon

[11] Patent Number: 5,788,852
[45] Date of Patent: Aug. 4, 1998

[54] PROCESS FOR PREVENTING ACCUMULATION OF CONTAMINANTS IN DENTAL SUCTION SYSTEMS

[76] Inventor: Howard Michael Mescon, 4141 N. Braeswood, Houston, Tex. 77025

[21] Appl. No.: 844,042

[22] Filed: Apr. 18, 1997

[51] Int. Cl.$^6$ .............................. C02F 1/50; A61C 17/06
[52] U.S. Cl. ..................... 210/749; 210/755; 210/764; 433/92; 422/28; 422/33; 422/37
[58] Field of Search ..................... 210/755, 764, 210/754, 749; 433/91, 92; 422/28, 33, 37

[56] References Cited

U.S. PATENT DOCUMENTS

| | | | |
|---|---|---|---|
| 3,733,143 | 5/1973 | Theis, Jr. | 415/80 |
| 4,054,998 | 10/1977 | Hesselgren | 32/33 |
| 4,087,198 | 5/1978 | Theis, Jr. | 415/82 |
| 4,328,101 | 5/1982 | Broden | 210/320 |
| 4,564,374 | 1/1986 | Hofmann | 55/57 |
| 4,963,094 | 10/1990 | Meyer | 433/95 |
| 5,018,971 | 5/1991 | Trawöger et al. | 433/92 |
| 5,188,530 | 2/1993 | Trawoger et al. | 433/92 |
| 5,282,744 | 2/1994 | Meyer | 433/92 |
| 5,484,282 | 1/1996 | Trawoger et al. | 433/92 |

*Primary Examiner*—Robert Popovics
*Attorney, Agent, or Firm*—Maryam Bani-Jamali

[57] ABSTRACT

This invention provides a method of operation of a suction system which provides simultaneous decontamination of the suction system and a process for preventing accumulation of contaminants in the suction system. Due to a vacuum created by a vacuum pump, waste mixtures are extracted and flow, via high-speed and low-speed vacuum lines, to a vacuum trap housing which contains a vacuum trap having a solid-collecting screen. Chemical agents, serving as water-soluble decontaminants and being preferably in the form of tablets, are placed in the vacuum trap housing on the solid-collecting screen and are placed adjacent to a number of other filters at positions selected to assure that each waste mixture comes into contact with and is treated by the chemical agents before leaving the suction system. Activation of the chemical agents by each waste mixture causes the decontamination of the waste mixture and the breakdown and decontamination of accumulations in the suction system. The treated waste mixture flows from the vacuum trap housing via a main vacuum line, connecting the vacuum trap housing to the vacuum pump, towards the vacuum pump which is preceded by the number of filters. When the flow of the waste mixture stops and the chemical agents become dry, the release of the chemical agents is automatically discontinued.

16 Claims, 4 Drawing Sheets

PROCESS FOR PREVENTING ACCUMULATION OF CONTAMINANTS IN DENTAL SUCTION SYSTEMS

BACKGROUND OF THE INVENTION

1. Field of the Invention

This invention relates to a method of operation of a suction system which provides simultaneous decontamination in the suction system. The invention also relates to a process for preventing accumulation of contaminants in the suction system.

2. Description of the Prior Art

A wide variety of chemicals, systems and processes have been developed for cleaning and decontaminating, as well as speeding up the cleaning and decontamination of, vacuum lines. A concentration area of applying such innovations has been the dental business. The application of this invention is described in the field of odontology, without being in any way limited thereto.

Modern dental care facilities use suction systems as waste disposal units for containing and disposing, in compliance with OSHA standards, waste mixtures comprising various liquids and solids originating from dental practice. Several patents have been issued in the past few decades that are focused on methods of operation of various dental suction systems uniquely designed for and processes for preventing accumulation of contaminants in such dental suction systems.

Trawöger et al., U.S. Pat. No. 5,188,530, registered on Feb. 23, 1993, discuss a process for preventing functional breakdowns in a dental suction unit by preventing the build-up of foam in the suction unit during dental treatment. Portions of a free-flowing additive (such as a decontaminant, a chemical agent and/or an anti-foam agent) have to be added periodically and repeatedly to at least a constituent of a liquid-solid mixture passing through the dental evacuation system. Trawöger et al. necessitate the addition of the additive either at definite intervals or at each transition between a working phase and a resting phase of the pump or by cancellation of the negative pressure in the suction unit.

Hesselgren, U.S. Pat. No. 4,054,998, issued on Oct. 25, 1977, patents a method and apparatus for continuously decontaminating a fluid medium that has been removed from an infectious area by passing the fluid medium through a decontaminating zone. A treating composition containing microbicidal substances is added in the decontaminating zone to the fluid medium. Hesselgren requires the arrangement of the treatment composition about the periphery of the flow path of the fluid medium in order to enable withdrawal of the microbicidal substance from the treatment composition.

However, some of these dental suction systems use complicated designs and have not been marketed to any considerable degree. A version of dental suction systems that has been considerably marketed and is being presently used in many, if not most, dental offices is a suction system for which the present invention is designed. The dental suction system includes a central vacuum system, with one vacuum pump being connected via a main vacuum line to and capable of providing vacuum for multiple operatories. In the operatories, high-speed and low-speed vacuum lines extend from the proximity of each dental chair to a vacuum trap housing. The high-speed and low-speed vacuum lines have an inlet wherefrom waste mixtures from a patient's mouth are sucked. Devices, such as aspirator tips, that necessitate vacuum conditions for operation are connected to the inlets of high-speed and low-speed vacuum lines. Each vacuum line runs within a suction tube that is connected to and has an outlet that opens into the vacuum trap housing. The waste mixture flows through the outlet of the high-speed and low-speed vacuum lines into the vacuum trap housing. A valve is positioned adjacent to the inlet of each high-speed and low-speed vacuum line and is automatically opened for the passage of fluids as soon as suction conditions commence. The vacuum trap housing is in turn connected via the main vacuum line to the vacuum pump. The main vacuum line runs through a narrow pipe (usually having a diameter of about ½" to ¾"), preferably comprising polyvinyl chloride (PVC). The vacuum pump has a propeller, which is encased and sealed in the pump. The vacuum pump generates a suction effect by using the propeller and water that is directed to the vacuum pump, wherein the sealed propeller rotates at an extremely high speed. (It should be noted that the water directed to the vacuum pump is obtained from city water lines that have no connection with the vacuum lines of the dental suction system.) The vacuum pump is preferably positioned in the vicinity of the operatories.

A device that is temporarily affixed to the inlet of a high-speed or low-speed vacuum line and that is needed for the dental treatment is positioned in the patient's mouth to remove liquids and solids (such as saliva, blood, rinsing liquids, fragments of tooth and filling material which collect during treatment) from the patient's mouth. Solids that flow out together with the liquids move through the high-speed or low-speed vacuum line towards the vacuum trap housing. A vacuum trap, that comprises a filter (referred to hereafter as a "solid-collecting screen") and a pin that holds down the solid-collecting screen in position, is used in the vacuum trap housing in order to prevent particles that are relatively large from leaving the vacuum trap housing towards the vacuum pump. Such larger particles include, but are not limited to, bone and tooth fragments, pieces of amalgam and some cellular material. (It should be noted that even though solid-collecting screens may be helpful in blocking the entrance of relatively large solid particles, the waste mixture moves fast enough to allow smaller solid particles in the waste mixture to pass through the solid-collecting screen and move from the vacuum trap housing towards the vacuum pump.) The larger solid particles are separated from the waste mixture and collected in the vacuum trap housing in which the solid particles are preferably sedimented upon the solid-collecting screen. The vacuum trap is removable and is cleaned at desired intervals or upon collection of a considerable amount of solid particles. The treated waste mixture, from which relatively large solid particles are removed but which is still contaminated, is directed via the main vacuum line to the vacuum pump. Contaminants from the waste mixture accumulate in the main vacuum line upon lapse of time. When treated waste mixtures pass through the main vacuum line, contaminants that remain from previous waste mixtures in the main vacuum line combine with one another and separate from the main-vacuum-line pipe. The treated waste mixture passes through a number of filters upon traveling through the main vacuum line. Such filters are used to collect solid particles that still exist in the waste mixture upon reaching the filters. The solid particles have either passed the vacuum trap along with the liquid or have remained, within the main-vacuum-line pipe, from previous streams of waste mixture. Upon opening of a return valve separator positioned in the main vacuum line, the waste mixture is then transferred into city sewage.

Because of the composition of the waste mixture to be suctioned and treated, many problems of typical conventional dental suction systems are related to cleaning and decontaminating some parts of the suction system through which the waste mixture flows. These problems create weak points, in reference to vacuum intensity, flow rate characteristics, efficiency and reliability of the suction system, which can lead to serious functional breakdowns. In order to decrease the rate of clogging up of the suction system, a chemical agent, dissolved in liquid in a separate container that is not connected to the suction system, has to be added regularly. High-speed and low-speed vacuum lines of the dental suction system are used to pull up enzymes in the dissolved chemical agents from the separate container. The time during which the enzymes are present in the vacuum trap housing is insufficient to allow efficient performance by existing chemical agents. Inefficient performance by the enzymes results in a build-up of accumulation in the dental suction system and causes a decrease in the efficiency of performance of the suction system. After the dental suction system is used for a short time, the suction system becomes saturated by accumulation and the resistance becomes so great for the vacuum pump that the functioning of the vacuum pump is disturbed, resulting in a breakdown of the vacuum pump. Some testings have indicated a 70% decrease in efficiency due to clogging up of the suction system when the period of dwelling of the enzymes in the vacuum trap housing is shortened. The decrease in the efficiency of performance of the dental suction system is approximately directly proportional to the volume of the main vacuum line that is clogged up with accumulation. Therefore, when 70% of the volume of the vacuum lines is clogged up with accumulation, there is approximately a 70% decrease in the efficiency of performance of the suction system. A decrease in efficiency of performance is accompanied by improper decontamination, unhygienic conditions and a waste of decontaminating chemical agents.

In order to improve hygienic conditions, the suction system is rinsed routinely with water-soluble chemical agents which serve as decontaminants. The use of high-speed and low-speed vacuum lines must be stopped at relatively short intervals and the suction system must be cleaned and decontaminated mechanically and by introduction, into the high-speed and low-speed vacuum lines, of cleaning and decontaminating chemical agents contained in a container that is separate from and has no connection with the dental suction system. Such process of decontamination is an unhygienic activity, since the waste mixture has a very high concentration of bacteria. In many cases, the vacuum trap is removed from the vacuum trap housing by a member of the staff in the dental office and carried to a wash basin, wherein the vacuum trap is cleaned by hand and/or with brushes. In such cases, the possibility that the bacteria existing in the vacuum trap reach individuals in the dental office is even higher. Also, the decontaminating process is very time-consuming. In addition, even though the suction system can be cleaned and decontaminated at the end of a working period (e.g. at the end of daily office hours or during work breaks), many times the dentist and some activities in the dental office must stop until the suction system is moved from the container of chemical agents and is set up again for use. It is extremely difficult for the dentist to work while the chemical agents are being added, since the dentist cannot use the high-speed and low-speed vacuum lines during the decontamination period. Furthermore, very frothy media cannot be sucked off.

The above-listed patents and many other similar inventions have been developed, some of which still exist in the market. However, no efficient and reliable decontamination is achieved by using chemical agents that are not in direct contact with the waste mixture or are from sources that are not directly connected to the dental suction system during operation of the suction system. In order to achieve acceptable hygienic results for protection of individuals in the dental office, the suction system must be continuously provided with microbicidal chemical agents during the entire time when the suction system is functioning. In addition, the chemical agents must be in direct contact with the waste mixture. Decontaminating waste mixtures of suction systems by placing decontaminating chemical agents, preferably in the form of tablets, within the vacuum trap housing and adjacent to any other filters in the suction system, wherein the chemical agents are used up only when being dissolved in the passing waste mixtures, is unique to the present invention.

SUMMARY OF THE INVENTION

A primary object of this invention is to devise a process in which waste mixtures that are passing through a suction system are decontaminated during operation of the suction system.

An additional object of this invention is to devise a process to prevent functional breakdowns, that result from excess accumulation of contaminants, of suction systems in order to extend maintenance intervals so that maintenance work is needed only when the whole unit is serviced.

Another object of this invention is to improve hygienic conditions in dental offices.

Yet another object of this invention is to minimize the consumption of chemical agents used for decontaminating suction systems.

Still another object of this invention is to minimize the amount of time that must be spent by individuals for decontaminating suction systems.

An additional object of this invention is to stabilize vacuum pressure in suction systems.

A final object of this invention is to increase the effectiveness, efficiency, reliability and life of suction systems.

Additional objects and advantages of the invention will be set forth in part in a detailed description which follows, and in part will be obvious from the description, or may be learned by practice of the invention.

The present invention provides a method of operation of a suction system which provides simultaneous decontamination of the suction system and a process for preventing accumulation of contaminants in the suction system. The invention focuses on the operation of high-speed and low-speed vacuum lines, a vacuum trap housing, a main vacuum line with a return valve separator, a vacuum pump and a number of filters that are generally used in dental suction systems. The vacuum pump is used for creating vacuum in the dental suction system. The waste mixture flows from the patient's mouth, via high-speed and low-speed vacuum lines, to the vacuum trap housing which contains a vacuum trap having a solid-collecting screen.

Some chemical agents, preferably in the form of tablets, serve as water-soluble decontaminants and are present in the vacuum trap housing at a position selected to assure that the waste mixture comes into contact with and is treated by any existing tablet before leaving the vacuum trap housing. The treated stream of waste mixtures flows from the vacuum trap housing via the main vacuum line, which connects the vacuum trap housing to the vacuum pump, towards the vacuum pump which is preceded by a number of filters. The stream of waste mixture, that is pulled via either a high-speed or a low-speed vacuum line, enters the vacuum trap housing at a speed that causes circulation of the waste mixture in the vacuum trap housing. The waste mixture, upon contacting and wetting any existing tablets, activates the chemical agents of the tablets. The chemical agents decontaminate the waste mixture and cause the breakdown and decontamination of accumulations in the vacuum trap housing and in the main vacuum line. The tablets continue to release the chemical agents as long as the tablets are in contact with the waste mixture.

When the flow of the waste mixture stops and the tablets dry, the release of the chemical agents by the tablets is automatically discontinued. The treated waste mixture is directed via the main vacuum line towards the vacuum pump. Some tablet are also positioned adjacent to each filter that precedes the vacuum pump, with each filter used to separate any remaining solid particles and the existing tablets applied to complement the decontamination commenced in the vacuum trap housing. Upon opening of the return valve separator positioned in the main vacuum line, the waste mixture passes through the number of filters and is then drained into city sewage lines.

It is to be understood that the descriptions of this invention are exemplary and explanatory, but are not restrictive, of the invention. Other objects and advantages of this invention will become apparent from the following specification and from any accompanying charts, tables, examples and drawings.

BRIEF DESCRIPTION OF CHARTS, TABLES, EXAMPLES AND DRAWINGS

Any accompanying charts, tables, examples and drawings which are incorporated in and constitute a part of this specification, illustrate examples of preferred embodiments of the invention and, along with the description, serve to explain the principles of the invention.

DETAILED DESCRIPTION OF THE PREFERRED EMBODIMENT

Preferred embodiments of the present invention are illustrated in any charts, tables, examples and drawings that are included.

Figure 1:
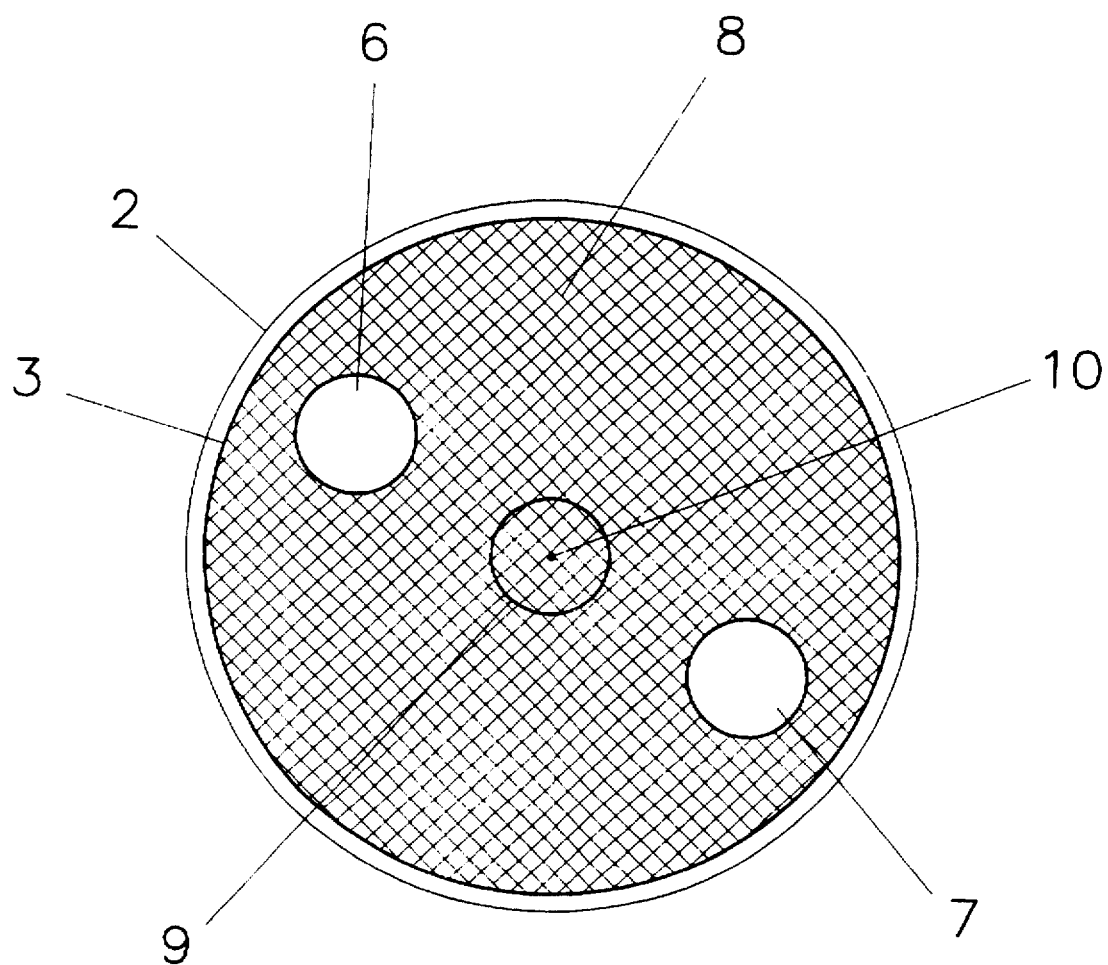
FIG. 1 shows a top view of a vacuum trap housing having a lid, with the lid having been removed.
Figure 2:
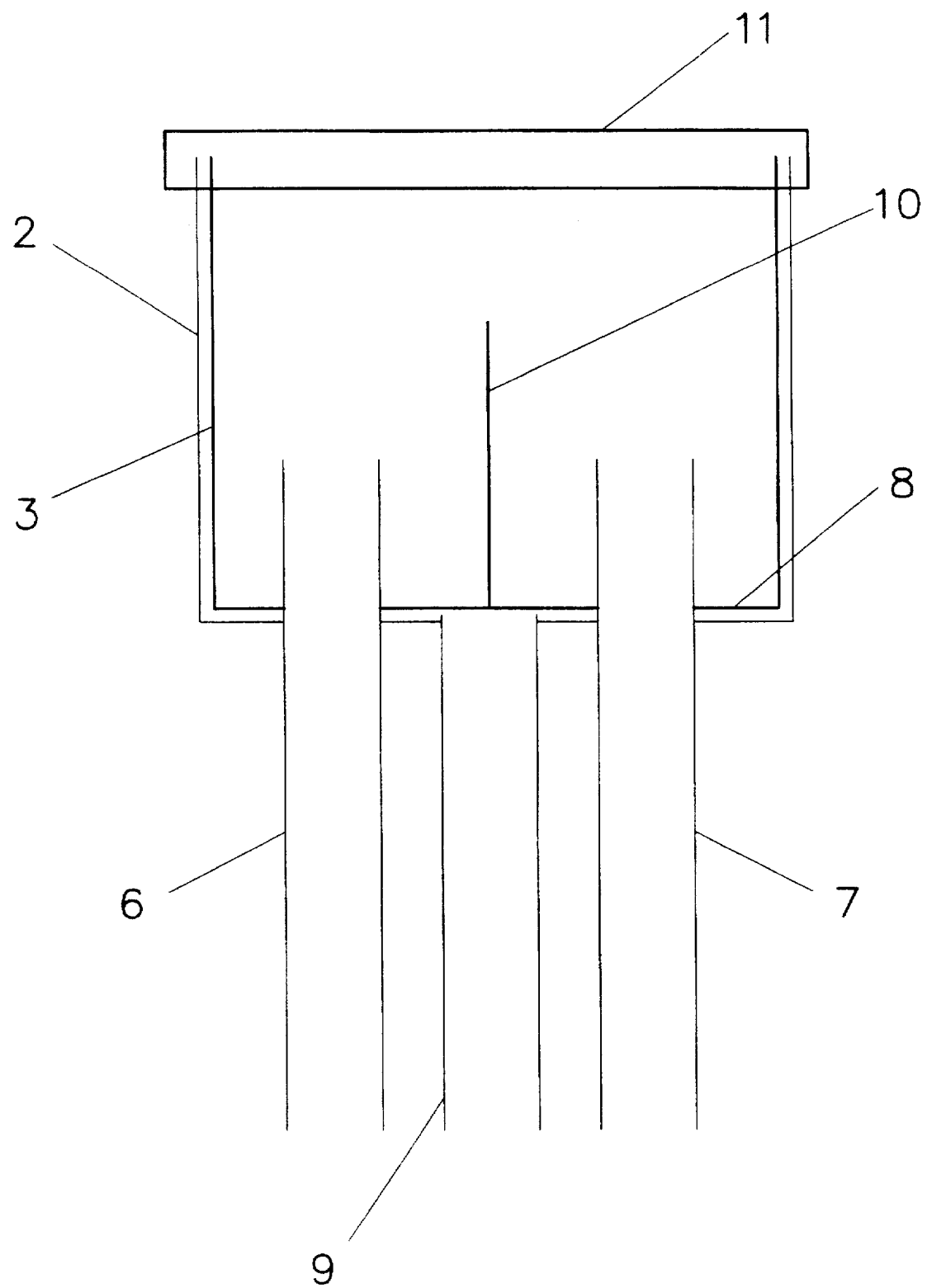
FIG. 2 shows a cross-sectional view of the vacuum trap housing of FIG. 2, with the lid being used.
Figure 3:
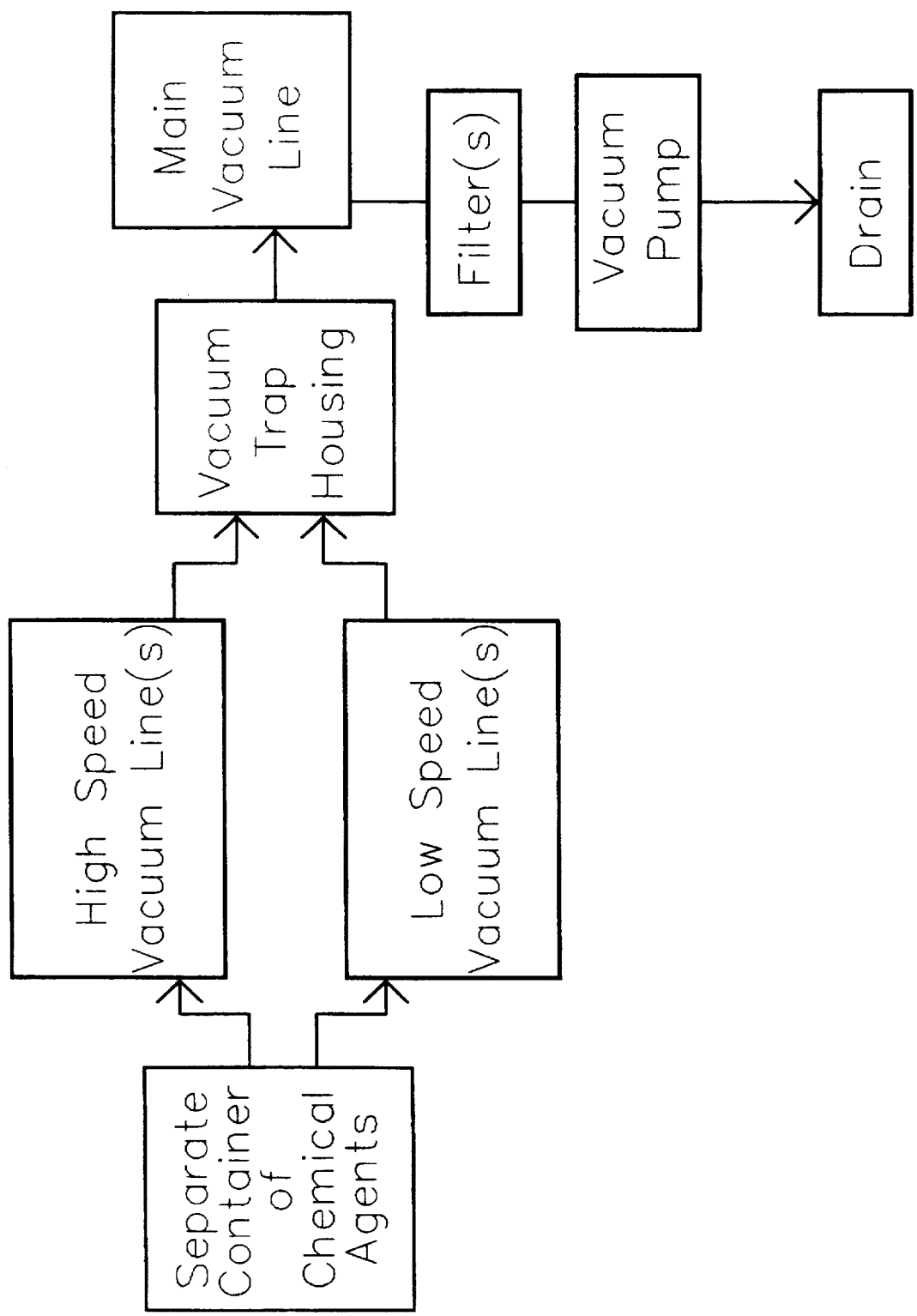
FIG. 3 shows a block diagram of components used for decontaminating a dental suction system wherein a decontaminating tablet is not used.
Figure 4:
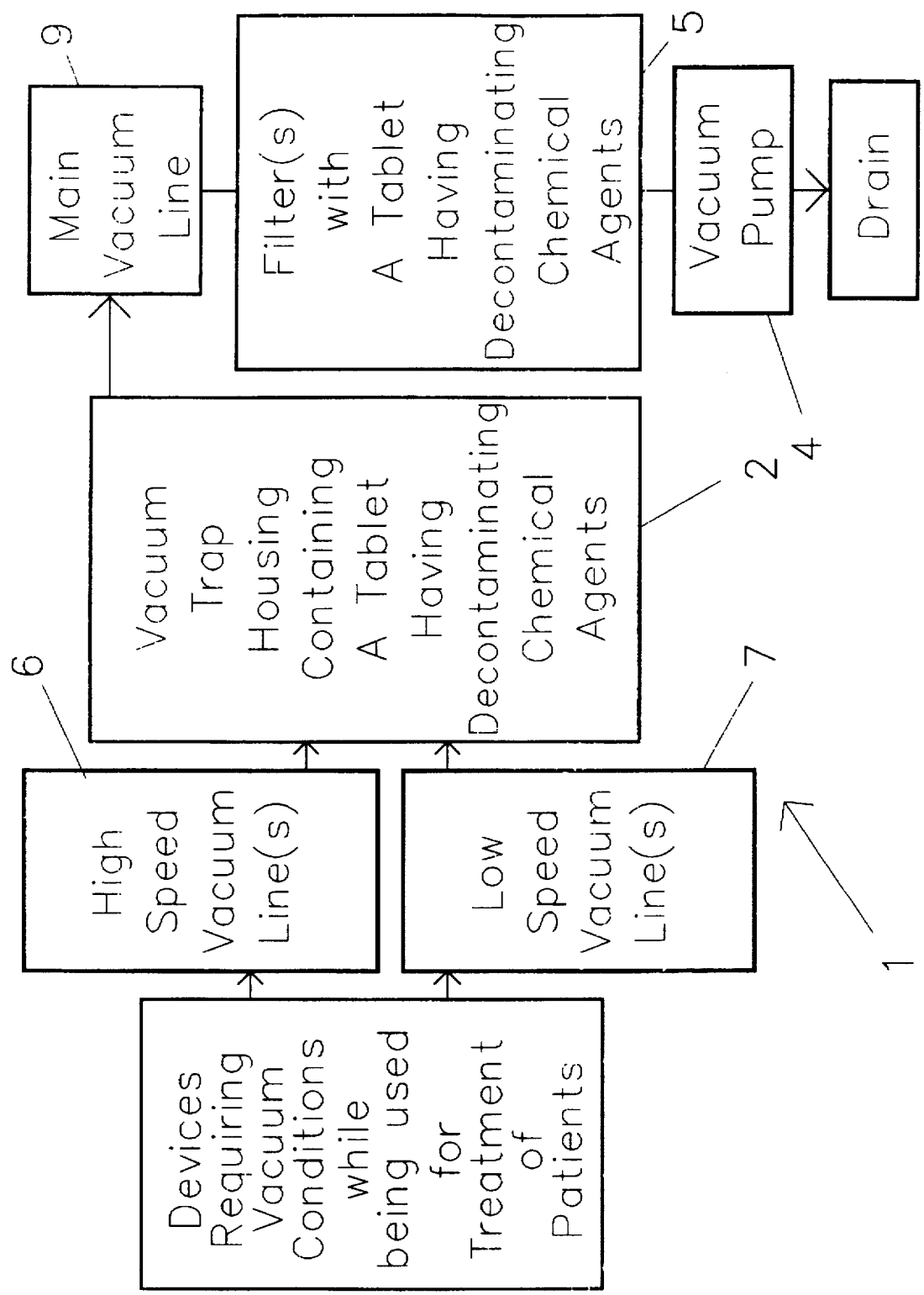
FIG. 4 shows a block diagram of components used for decontaminating the dental suction system, of FIG. 3, wherein a decontaminating tablet is used.

The present invention relates to a method of operation of a dental suction system 1 which provides simultaneous decontamination of the suction system 1 and to a process for preventing accumulation of contaminants in the suction system 1. The structure of the dental suction system 1 of the present invention is identical to the structure of the already described, existing dental suction system 1. (Please refer to FIG. 1 to FIG. 4, inclusively.) The contaminants originate from a waste mixture that is suctioned out of a patient's mouth by a vacuum created within the suction system 1. The suction system 1 comprises vacuum lines (high-speed and low-speed vacuum lines 6,7, as well as a main vacuum line 9), a vacuum trap housing 2 containing a vacuum trap 3, a vacuum pump 4 and a number of filters 5. In a preferred embodiment, a high-speed vacuum line 6 and a low-speed vacuum line 7, which each have an inlet and an outlet and run within a suction tube, extend from the proximity of a dental chair to the vacuum trap housing 2. In addition, one solid-collecting screen 8 (i.e. a filter 5 in the vacuum trap housing 2), one vacuum pump 4, one filter 5 preceding the vacuum pump 4 and a main vacuum line 9 are used. The main vacuum line 9 has a small diameter and a return valve separator and extends underground between the vacuum trap housing 2 and the vacuum pump 4.

The vacuum pump 4 is used for creating vacuum in the suction system 1 in order to draw the waste mixture from the patient's mouth by using a medical device, positioned in the patient's mouth and connected to the inlet of either a high-speed or a low-speed vacuum line 6,7. The amount of vacuum is adjusted to be sufficient to draw the waste mixture through the suction system 1. Preferably, the vacuum trap housing 2 is cylindrical in shape and is positioned at a short distance from the inlet of the high-speed and low-speed vacuum lines 6,7. A valve, that is adjacent to the inlet of each high-speed vacuum line 6 and of each low-speed vacuum line 7, is automatically opened as soon as suction conditions commence. The high-speed and low-speed vacuum lines 6,7 protrude into the vacuum trap housing 2 while the connection to the main vacuum line 9 starts at the bottom of the vacuum trap housing 2. The vacuum trap 3 is removable and replaceable and has a pin 10 that facilitates pulling out and positioning of the vacuum trap 3. The vacuum trap 3 can be removed and replaced by a new vacuum trap 3 when a new set of tablets are being added to the vacuum trap housing 2. The pin 10 serves a dual function: holding down the solid-collecting screen 8, preferably at a central location, and being a means for grabbing when the solid-collecting screen 8 is being pulled out of or placed in the vacuum trap housing 2. The vacuum trap housing 2 includes a lid 11 which can be easily removed and repositioned when desired. The vacuum trap 3 is sized to fit tightly in the vacuum trap housing 2. The solid-collecting screen 8 rests at the bottom of the vacuum trap 3 and neighbors the connection to the main vacuum line 9. A major portion of the main vacuum line 9 is underground. Preferably, the main vacuum line 9 has a diameter of between approximately ½ inch to approximately ¾ inch. The vacuum pump 4 may be operated by a small motor, yet it can effectively serve the suction systems 1 from several dental operatories. The vacuum pump 4 has a propeller that is encased and sealed in the vacuum pump 4 and that is the propulsion source for the suction system 1. A stream of water, which does not come into contact with the waste mixture, cooperates with the propeller such that the propeller rotates at a speed that is high enough to enable the production of a desired vacuum stage. The propeller of the vacuum pump 4 rotates at a speed that is fast enough to create sufficient suction at high-speed and low-speed vacuum lines 6,7. The vacuum intensity of the suction system 1 is stabilized in the vacuum trap housing 2. The vacuum intensity is substantially constant as flow volume increases, up to the capacity of the vacuum pump 4, so that the vacuum intensity remains substantially constant whether high-speed and low-speed vacuum lines 6,7 of one or more suction systems 1 are connected to the main vacuum line 9 and, therefrom, to the vacuum pump 4. The vacuum, created by the vacuum pump 4, forces the waste mixture to be drawn towards the vacuum trap housing 2 and the treated fluid to be drawn towards the vacuum pump 4 in a defined flow direction. The treated waste mixture passes through the number of filters 5, which are positioned adjacent to the vacuum pump 4, upon traveling through the main vacuum line 9. Such filters 5 are used to collect solid particles that still exist in the waste mixture upon reaching the filters 5. The solid particles have either passed the vacuum trap 3 along with the liquid or have remained, within the main vacuum line 9, from previous streams of waste mixture. In addition, the treated waste mixture that leaves the vacuum trap housing 2 is still decontaminated when moving through the main vacuum line 9. Some contaminants may remain in the main vacuum line 9. However, when following waste mixtures pass through the main vacuum line 9, the chemical agents that are present in the waste mixtures result in the separation of the accumulated contaminants from the main vacuum line 9. Some tablets are also positioned adjacent to each filter 5 that precedes the vacuum pump 4. Each filter 5 is used to separate any remaining solid particles and each tablet is applied to complement the decontamination commenced in the vacuum trap housing 2. Upon opening of the return valve separator positioned in the main vacuum line 9, the waste mixture passes through the number of filters 5 and is then drained into city sewage lines.

The structure of the dental suction system 1 used in the present invention is not new. The method of operation of the dental suction system 1 and the process for preventing accumulation of contaminants in the dental suction system 1 are novel and form the essence of the present invention. Under vacuum conditions created by the vacuum pump 4, the waste mixture is drawn either through a high-speed or through a low-speed vacuum line 6,7 to the vacuum trap 3 in the vacuum trap housing 2. Within the vacuum trap housing 2, the solid-collecting screen 8 serves to minimize the passage of relatively large particles into the main vacuum line 9. The vacuum trap housing 2 also serves as a decontamination zone in which the waste mixture is treated with at least one chemical agent which is a microbicide. (The singular form of the phrase "chemical agents" will be used for simplicity, without any limitation on the number of chemical agents.)

A major role in the application of the process is played by the chemical agent. The chemical agent is preferably in the form of a tablet and is placed in the vacuum trap housing 2 at a position selected to assure that the waste mixture comes into direct contact with the tablet before leaving the vacuum trap housing 2. (It should be emphasized that the chemical agents can be applied in other forms as well. Although use of chemical agents in the form of tablets has yielded the most efficient results, the chemical agents may be used in other forms, e.g. as gels.) Tablets of different formulations and strengths are being presently used. A preferred version of the tablet comprises a quaternary ammonium salt, such as n-alkyl dimethyl benzyl ammonium chloride. The tablets consist of pre-measured doses on which the strength, speed and effect of cleaning and decontamination depend. An essential advantage of using the chemical agent in tablet form is that the tablets are fast-acting and are released gradually over a period of time. Upon being activated, the tablets commence the process of decontamination in the vacuum trap housing 2 and in the main vacuum line 9, yielding an open, clean and decontaminated main vacuum line 9. By being released over time and only when needed, each tablet could be effective for several days. When one tablet is used up, another tablet is added to the suction system 1 by being positioned in the vacuum trap housing 2 adjacent to the solid-collecting screen 8. Preferably, two tablets are positioned in the vacuum trap housing 2 adjacent to the solid-collecting screen 8. One tablet, that has a larger concentration of chemical agent, is used to boost the suction system 1. The tablet is activated only when it comes into contact with a fluid and is hydrated. When an amount of water is added to the vacuum trap housing 2, the tablet is activated such that the suction system 1 is boosted and one period of cleaning and decontamination occurs prior to the flow of waste mixtures from the patient's mouth. One gallon of water would be helpful to activate the tablet that is being most commonly used at the present. The other tablet is also positioned on the solid-collecting screen 8 of the vacuum trap 3. The second tablet follows up on the cleaning and decontamination process of the first, stronger tablet. The second tablet is activated when contacted by the waste mixture. Since the pin 10 that holds the solid-collecting screen 8 in place is preferably positioned in the center of the solid-collecting screen 8, if the diameter of the tablet is larger than the radius of the solid-collecting screen 8, the tablet can be broken into pieces and, then, positioned on the solid-collecting screen 8. Although upon being contacted by fluids the tablet is immediately activated and releases the chemical agent, the tablet is stable and can be safely and easily transported and handled when in solid state. No matter where the tablet is positioned and of what size is the tablet, the tablet becomes activated as soon as it comes into contact with a fluid and is hydrated. Naturally, when one tablet is broken down into pieces of smaller size, a larger surface area of the tablet comes in contact with the waste mixture and there is a faster consumption of the chemical agent.

However, using tablets, instead of free-flowing additives, provides a more efficient system and a decrease in consumption of the chemical agent. Tablets last longer and are more economical than free-flowing additives since only suitable quantities of the water-soluble tablets are used up by the departing waste mixture and the usage is only when the suction system 1 is in function. When the suction system 1 is not being used, the tablet remains dry and is not consumed since it is not dissolved in any fluids. The free-flowing feature of many existing additives is responsible for a major disadvantage of using such additives. Being free-flowing, the additives remain in the suction system 1 for a shorter period of time. Free-flowing additives have to be added repeatedly upon each transition from a working phase to a resting phase of the suction system 1 (several dozens of such transitions occur during each working day in many presently-used systems).

The location of the tablet is essential to the improvements resulting from the present invention since some major goals of the present invention are to minimize the consumption of the chemical agent used for cleaning and decontaminating the suction system 1, to minimize the amount of time needed to clean and decontaminate the suction system 1, to assure that the waste mixtures are decontaminated during the operation of and within the suction system 1 and to improve the hygienic conditions in the dental office. The narrowness of the main vacuum line 9, the composition of the main vacuum line 9 (i.e. polyvinyl chloride—PVC) and the position of the number of filters 5 in contact with the main vacuum line 9 serve as ideal features for collection and coagulation of contaminants, thus resulting in the clogging of the main vacuum line 9 and of the number of filters 5. The treated fluid stream, resulting from cleaning and decontaminating the waste mixture in the vacuum trap housing 2, moves via the main vacuum line 9 to the vacuum pump 4.

With the vacuum trap housing 2 immediately preceding the main vacuum line 9, the positioning of the tablet in the vacuum trap housing 2 causes a minimization of the passage of contaminants existing in the waste mixture from the vacuum trap housing 2 to the main vacuum line 9 and, therefore, to the number of filters 5 and to the vacuum pump 4. (Please refer to FIG. 4.) By minimizing the entrance of contaminants into the main vacuum line 9, the rate of coagulation of contaminants in the suction system 1 is considerably slower and the possibility of malfunctioning of the dental suction system 1 is essentially nullified. A decrease in the amount of contaminants passing through the main vacuum line 9 results in an increase in the operation efficiency of the suction system 1. The speedier is the blocking of the main vacuum line 9, the shorter is the period between breakdowns of the suction system 1 and between required maintenance work, the more unstable is the vacuum pressure in the suction system 1 and the lower are the effectiveness, efficiency, reliability and life of the suction system 1. Because of the composition of the waste mixture, if there is an excess accumulation of contaminants, it is not possible to keep the dental suction system 1 in a serviceable state unless its components are thoroughly cleaned and decontaminated after each occasion when the waste mixture is drained off. Obviously, it is not practical to repeatedly reach, decontaminate and clean the main vacuum line 9, which is underground.

When the chemical agent is in the suction system 1 during the operation of the suction system 1, there is no need to stop the use of the suction system 1 in order to decontaminate the suction system 1. The decontamination of the suction system 1 occurs every time that a waste mixture stream passes through the vacuum trap 3 (i.e. during the use of the suction system). The waste mixture is treated by the chemical agent within the vacuum trap housing 2 and before the waste mixture enters the main vacuum line 9. The fact that the tablet is included within the suction system 1 during the medical application of the suction system 1 results in a very intimate contact occurring between the dispersed contaminants and the decontaminating chemical agent. Removing and replacing the main vacuum line 9 is not possible without reaching underground. On the other hand, the vacuum trap housing 2 is usually either in or adjacent to the operatory and, thus, the vacuum trap 3 is very easily removed to be cleaned or replaced. Therefore, there is a considerable decrease in the amount of time needed for cleaning and decontaminating the suction system 1. In addition, the unhygienic conditions resulting from the cleaning and decontamination of the suction system 1, by using a separate container by an individual in the dental office, are eliminated upon application of the present invention. Instead of stopping the dental suction system 1 for each decontamination process, a tablet is always present in the vacuum trap housing 2 and is automatically triggered and automatically dispersed into the waste mixture when contacted by the waste mixture or by any other fluid. The stream of waste mixture, that is pulled up through the high-speed and low-speed vacuum lines 6,7, enters the vacuum trap housing 2 at a speed that causes circulation of the waste mixture in the vacuum trap housing 2. The circulating waste mixture comes into contact with the tablet that, upon becoming wet, is activated and starts releasing the chemical agent in the vacuum trap housing 2. Thus, the decontamination of the waste mixture commences. The chemical agent also causes the breakdown of unwanted accumulations in the vacuum trap housing 2. A portion of the released chemical agent, that dissolves in the waste mixture leaving the vacuum trap housing 2, travels through the main vacuum line 9 and causes the breakdown of unwanted accumulations in the main vacuum line 9. Until the tablet is in contact with the waste mixture, the tablet continues to disperse the chemical agent. As the amount of the waste mixture contacting the tablet decreases, the rate of dispersion of the chemical agent of the tablet decreases. When the flow of the waste mixture stops, the tablet becomes dry and the dispersion of the chemical agent stops. Thus, the present invention introduces a cycle of activation, dispersion and deactivation of the tablet based upon the amount of fluid existing in the vacuum trap housing 2. The cycle is automatic and is triggered by a contact between the tablet and the waste mixture. When the suction system 1 is not being used, the tablet is not dissolved either. Therefore, the present invention is economically advantageous. As a result, there is neither a need for intervention in the treatment process of patients nor in the cleaning and decontamination process of the suction system 1. With the tablet becoming automatically activated, the contaminants of the waste mixture are immediately treated in the vacuum trap housing 2 before entering the main vacuum line 9. There is no need for opening up and exposing individuals in the dental office to contaminants. By requiring no supervision during the application of the tablet, there is a saving in the required labor fees for maintaining the suction system 1.

Since the waste mixture is in direct contact with the chemical agent from the vacuum trap housing 2 during passage through the suction system 1 and for a longer period and since there is no time gap between the passage of the contaminants and of the chemical agent through the suction system 1, there is an extremely low opportunity for contaminants to coagulate within the suction system 1. (Please compare FIG. 3 with FIG. 4.)

The present invention uses the same apparatus as many existing dental suction systems. The novelty of the invention lies in two essential features. The method of operation of the dental suction system 1 provides simultaneous decontamination of the suction system 1. In addition, the process that is introduced prevents accumulation of contaminants and decontaminates the waste mixture automatically and without requiring the intervention of an individual. The improvements presented in the efficiency and performance of the suction system 1 result from the application of the decontaminating chemical agent within the suction system 1 such that the chemical agent is only used when activated by the waste mixture, such that the waste mixture is decontaminated before entering the main vacuum line 9, such that the suction system 1 can operate and the desired medical devices can be used while the waste mixture is being treated and such that there is no time gap between the passage of the waste mixture and the passage of the chemical agent through the main vacuum line 9. Since no supervision is required during application of the chemical agent to the operation of the suction system 1, there is a noticeable decrease in the amount of labor required for cleaning and decontaminating the suction system 1. Since the chemical agent is used to prevent coagulation of contaminants in the suction system 1, if there is no functional breakdown in the suction system 1, the only required task would be adding any desired number of new tablets when the original tablets are used up. If the tablet is at a position that can be seen during the operation of the suction system 1, the need for adding a new tablet can be very easily established by using colored tablets. As soon as the color, in the waste mixture, that is attributed to the tablet fades away, a new tablet must be added.

Accumulated waste components of the waste mixture can be disposed of in various ways. Chemicals and solid ingredients that are accumulated in the vacuum trap housing 2 during cleaning and decontamination of the waste mixture can be removed by moving the vacuum trap 3, including the solid-collecting screen 8, out of the suction system 1 for disposal. The solid matter accumulated on the solid-collecting screen 8 may include, in addition to the larger particles from the waste mixture, residues from tablets used in the vacuum trap housing 2.

The chemical agent used for the decontamination of the suction system 1 is non-toxic, non-corrosive and simple to use. The application of the chemical agent does not result in any rusting and lengthens the life of the vacuum pump 4 and of the main vacuum line 9. Vacuum pressure is stabilized and desired vacuum intensity is achieved. The application of the invention is much simpler than the operation of existing dental suction systems. Since the dispersion rate of the tablet is slower than the dispersion rate of existing cleaning and decontaminating agents, there is a decrease in expenses for cleaning and decontaminating the waste mixture. The efficiency of cleaning and decontaminating and the reliability of the suction system 1 are enhanced.

It should be emphasized that the present invention is not limited to the dental practice. The improvements can also be used for other medical practices (e.g. surgery) where a suction system is used. The improvements may even have an application in non-medical areas where a similar suction system comes into contact with contaminants that can decrease the efficiency of the operation. Different chemical agents may be used for different contaminants. However, the essential features of the invention could be applied for each case.

Certain objects are set forth above and made apparent from the foregoing description, drawings and examples. However, since certain changes may be made in the above description, drawings and examples without departing from the scope of the invention, it is intended that all matters contained in the foregoing description, drawings and examples shall be interpreted as illustrative only of the principles of the invention and not in a limiting sense. With respect to the above description and examples then, it is to be realized that any descriptions, drawings and examples deemed readily apparent and obvious to one skilled in the art and all equivalent relationships to those stated in the examples and described in the specification or illustrated in the drawings are intended to be encompassed by the present invention.

Further, since numerous modifications and changes will readily occur to those skilled in the art, it is not desired to limit the invention to the exact construction and operation shown and described, and accordingly, all suitable modifications and equivalents may be resorted to, falling within the scope of the invention. It is also to be understood that the following claims are intended to cover all of the generic and specific features of the invention herein described, and all statements of the scope of the invention which, as a matter of language, might be said to fall in between.

What is claimed as invention is:

1. A method of operation of a suction system comprising high-speed and low-speed vacuum lines each having an inlet and an outlet, a vacuum trap housing containing a vacuum trap that has a solid-collecting screen and being connected to the outlet of the high-speed and low-speed vacuum lines, a vacuum pump, a main vacuum line extending between the vacuum trap housing and the vacuum pump and a number of filters positioned adjacent to the vacuum pump, said method providing simultaneous decontamination of the suction system during the operation of and each time a waste mixture is passing through the suction system and comprising:

(a) placing a number of chemical agents, serving as decontaminants, above the vacuum trap in the vacuum trap housing at a position where each extracted waste mixture comes into contact with the number of chemical agents before exiting the vacuum trap housing;

(b) placing a number of chemical agents serving as decontaminants in front of each filter, preceding the vacuum pump, at a position where each extracted waste mixture comes into contact with the number of chemical agents before exiting the suction system;

(c) applying the vacuum pump to create vacuum conditions in the suction system in order to withdraw each waste mixture through the high-speed or low-speed vacuum lines and into the vacuum trap housing at a speed that causes circulation of the waste mixture in the vacuum trap housing;

(d) repeating step (c) as often as desired until all chemical agents positioned in the vacuum trap housing or positioned adjacent to any filter are used up, at which time step (a) is repeated if all chemical agents in the vacuum trap housing are used up and step (b) is repeated for any filter which lacks chemical agents;

(e) repeating step (d) as often as desired until the solid-collecting screen or any filter is to be removed and replaced, at which time step (a) is repeated for the newly-positioned solid-collecting screen and step (b) is repeated for any newly-positioned filter; and (f) repeating steps (d) and (e) as often as desired without risk of accumulation of contaminants in the suction system and without requiring any other version of decontamination of the suction system;

such that when each waste mixture comes into contact with and hydrates any existing chemical agent in the suction system, the chemical agent is automatically activated to decontaminate the waste mixture and to cause the breakdown of unwanted accumulations in the suction system; and such that the chemical agents are automatically dispersed, when contacted by each waste mixture, into the waste mixture until the flow of the waste mixture is discontinued and, thus, the chemical agents become dry and the consumption of the chemical agents stops.

2. The method of operation of the suction system according to claim 1, wherein the chemical agents are in the form of tablets.

3. The method of operation of the suction system according to claim 2, wherein an amount of water is added to the tablets, with the tablets serving to boost the suction system.

4. The method of operation of the suction system according to claim 2, wherein as the amount of each waste mixture contacting the tablet decreases, the rate of dispersion of the chemical agent in the waste mixture decreases and, thus, the consumption of the chemical agent decreases until the tablet becomes dry.

5. The method of operation of the suction system according to claim 1, wherein the chemical agent comprises a quaternary ammonium salt.

6. The method of operation of the suction system according to claim 5, wherein the chemical agent comprises n-alkyl dimethyl benzyl ammonium chloride.

7. The method of operation of the suction system according to claim 1, wherein the vacuum trap is removed and is replaced by a new vacuum trap when any additional chemical agents are needed in the vacuum trap housing and wherein any filter which is to be provided with any additional chemical agents is removed and is replaced by a new filter.

8. The method of operation of the suction system according to claim 1, wherein an additional amount of chemical agent is added upon a change in color, which is associated with the chemical agent, of the waste mixture.

9. A process for preventing accumulation of contaminants in a suction system through which extracted waste mixtures flow, said process comprising:

(a) placing a number of chemical agents, serving as decontaminants, above a vacuum trap in a vacuum trap housing at a position where each extracted waste mixture comes into contact with the number of chemical agents before exiting the vacuum trap housing;

(b) placing a number of chemical agents serving as decontaminants in front of each filter, preceding a vacuum pump, at a position where the extracted waste mixture comes into contact with the number of chemical agents before exiting the suction system;

(c) applying the vacuum pump to create vacuum conditions in the suction system in order to withdraw each waste mixture through high-speed or low-speed vacuum lines , that lead to the vacuum trap housing, into the vacuum trap housing at a speed that causes circulation of the waste mixture in the vacuum trap housing;

(d) repeating step (c) as often as desired until all chemical agents positioned in the vacuum trap housing or positioned adjacent to any filter are used up, at which time step (a) is repeated if all chemical agents in the vacuum trap housing are used up and step (b) is repeated for any filter which lacks chemical agents;

(e) repeating step (d) as often as desired until the vacuum trap or any filter is to be removed and replaced, at which time step (a) is repeated for the newly-positioned vacuum trap and step (b) is repeated for any newly-positioned filter; and (f) repeating steps (d) and (e) as often as desired without risk of accumulation of contaminants in the suction system and without requiring any other version of decontamination of the suction system;

such that when the waste mixture comes into contact with and hydrates any existing chemical agent in the vacuum trap housing, the chemical agent is automatically activated to decontaminate the waste mixture and to cause the breakdown of unwanted accumulations in the vacuum trap housing;

such that any portion of the chemical agents that is dissolved in the waste mixture that leaves the vacuum trap housing, while continuing the decontamination of the waste mixture, causes the breakdown and decontamination of unwanted accumulations in a main vacuum line that connects the vacuum trap housing to the vacuum pump;

such that when the waste mixture comes into contact with and hydrates any existing chemical agent positioned before each filter, the chemical agent is automatically activated to decontaminate the waste mixture and to cause the breakdown of unwanted accumulations before the waste mixture passes through the filter and is transferred into sewage lines; and such that the chemical agents are automatically dispersed, when contacted by each waste mixture, into the waste mixture until the flow of the waste mixture is discontinued and, thus, the chemical agents become dry and the consumption of the chemical agents stops.

10. The process of claim 9, wherein the chemical agents are in the form of tablets.

11. The process of claim 10, wherein an amount of water is added to the tablets, with the tablets serving to boost the suction system.

12. The process of claim 10, wherein the process includes a cycle of activation, dispersion and deactivation of the chemical agent based upon the amount of waste mixture existing in the suction system, such that as the amount of each waste mixture contacting the tablet decreases, the rate of dispersion of the chemical agent in the waste mixture decreases and, thus, the consumption of the chemical agent decreases until the tablet becomes dry.

13. The process of claim 9, wherein the chemical agent comprises a quaternary ammonium salt.

14. The process of claim 13, wherein the chemical agent comprises n-alkyl dimethyl benzyl ammonium chloride.

15. The process of claim 9, wherein the vacuum trap is removed and is replaced by a new vacuum trap when an additional amount of chemical agents is being placed in the vacuum trap housing and wherein any filter which is to be provided with an additional amount of chemical agents is removed and is replaced by a new filter.

16. The process of claim 9, wherein an additional amount of chemical agent is added upon a change in color, which is associated with the chemical agent, of the waste mixture.

* * * * *